United States Patent
Allen et al.

[11] Patent Number: 5,216,017
[45] Date of Patent: Jun. 1, 1993

[54] PYRROLO[2,3-B]INDOLE-KETONES AND ANALOGS

[75] Inventors: Richard C. Allen, Flemington; Denise M. Flanagan, Bridgewater, both of N.J.

[73] Assignee: Hoechst-Roussel Pharmaceuticals Incorporated, Somerville, N.J.

[21] Appl. No.: 765,780

[22] Filed: Sep. 26, 1991

Related U.S. Application Data

[63] Continuation-in-part of Ser. No. 521,953, May 11, 1990, abandoned.

[51] Int. Cl.$^5$ .................... C07D 487/04; A61K 31/40
[52] U.S. Cl. ...................................... 514/411; 548/429
[58] Field of Search .......................... 548/424; 514/411

[56] References Cited

U.S. PATENT DOCUMENTS 4,791,107  12/1988  Hamer ................................ 514/322
4,971,992  11/1990  Glamkowski ........................ 548/429

FOREIGN PATENT DOCUMENTS 154864  9/1985  European Pat. Off. .

OTHER PUBLICATIONS

Julian, J.A.C.S. 57, 563, 755 (1935).
Tamguchi, Chem. Pharm. Bull 31 (6) 1856 (1963).
Kosugi, Chem. Letters 1982, 939-940.

Primary Examiner—Mark L. Berch
Attorney, Agent, or Firm—Elliott Korsen

[57] ABSTRACT

This invention relates to pyrrolo[2,3-b]indole ketones of the formula

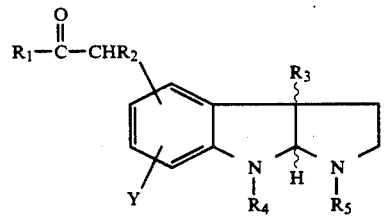

where $R_1$ is loweralkyl, aryl or arylloweralkyl; $R_2$ is hydrogen, halogen or loweralkyl; $R_3$ is hydrogen or loweralkyl; $R_4$ is loweralkyl or arylloweralkyl; $R_5$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy; the pharmaceutically acceptable addition salts thereof, and where applicable, the geometric and optical isomers and racemic mixtures thereof. The compounds of this invention are useful in the treatment of memory impairment characterized by a cholinergic deficit such as that associated with electroshock-induced amnesia and Alzheimer's disease and other senile dementia.

4 Claims, No Drawings

PYRROLO[2,3-B]INDOLE-KETONES AND ANALOGS

This application is a continuation-in-part of pending U.S. patent application Ser. No. 521,953 filed May 11, 1990 abandoned.

This invention relates to pyrrolo[2,3-b]indole-ketones of the formula

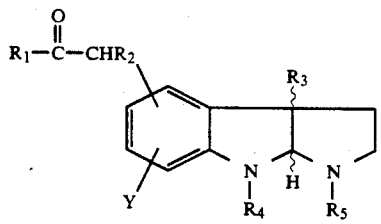

where $R_1$ is loweralkyl, aryl or arylloweralkyl; $R_2$ is hydrogen, halogen or loweralkyl; $R_3$ is hydrogen or loweralkyl; $R_4$ is loweralkyl or arylloweralkyl; $R_5$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy; the pharmaceutically acceptable addition salts thereof, and where applicable, the geometric and optical isomers and racemic mixtures thereof. The compounds of this invention are useful in the treatment of memory impairment characterized by a cholinergic deficit such as that associated with electroshock-induced amnesia and Alzheimer's disease and other senile dementia.

Throughout the specification and appended claims, a given chemical formula or name shall encompass all geometric and optical isomers and racemic mixtures where such isomers and mixtures exist.

In the above definitions, the term "lower" means the group it is describing contains from 1 to 6 carbon atoms. The term "alkyl" refers to a straight or branched chain hydrocarbon of 1 to 22 carbon atoms, containing no unsaturation, e.g., methyl, ethyl, propyl, isopropyl, 2-butyl, neopentyl, n-hexyl, etc.; the term "arylloweralkyl" refers to a monovalent substituent which consists of an "aryl" group, e.g., phenyl, o-tolyl, m-methoxyphenyl, etc., as defined by the formula

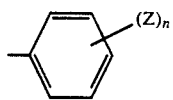

where Z is as defined below, and n is an integer of 1 to 3, linked through a loweralkylene group having its free valence bond from a carbon of the loweralkylene group, and having a formula of

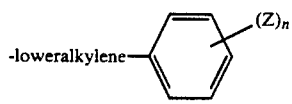

where Z is hydrogen, halogen, loweralkyl, loweralkoxy, trifluoromethyl, nitro and amino; the term "alkylene" refers to a bivalent radical of the lower branched or unbranched alkyl group it is derived from having valence bonds from two terminal carbons thereof, e.g., methylene (—$CH_2$—), ethylene (—$CH_2CH_2$—), propylene (—$CH_2CH_2CH_2$—), isopropylene

$(CH_3CHCH_2—)$, or etc.; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; the term "alkenyl" refers to a hydrocarbon group of 1 to 22 carbon atoms having one or more carbon-carbon double bonds, e.g., ethene, propene, butene, etc.; the term "alkynyl" refers to a hydrocarbon group of 1 to 22 carbon atoms having one or more carbon-carbon triple bonds, e.g., acetylene, propyne, butyne, pentyne, etc.; and the term "halogen" refers to a member of the halogen family consisting of fluorine, chlorine, bromine and iodine.

The compounds of this invention are prepared in the following manner. The substituents $R_1$, $R_2$, $R_3$, $R_4$, $R_5$ and Y are as defined above unless indicated otherwise.

In structural formulas depicting compounds involved in this invention, heavy lines (—) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines (⋯) signify that the two substituents are below the average plane of the three-ring system, and wavy lines (~) signify that the two substituents are both either above or below said average plane. Because of conformational constraints, the two-substituents at the 3a- and 8a-positions must both be above said average plane or both be below said average plane. Thus, in formula I, the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis.

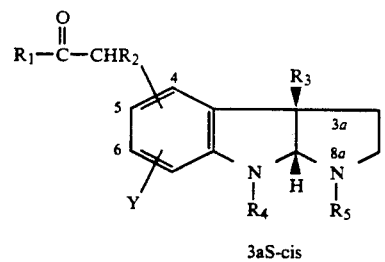

3aS-cis

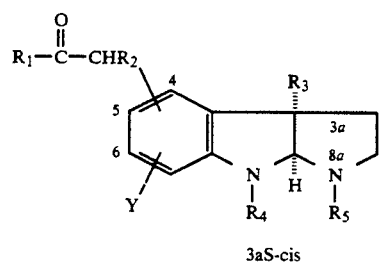

3aS-cis

Throughout the specification and the appended claims, when the inventors intend to designate in a single formula that the compound is 3aS-cis or 3aR-cis, or a racemic or other mixture of the two, that formula will contain wavy lines as in formula I.

It is the intent of the present inventors to claim both of said cis isomers, namely, 3aS-cis isomer and 3aR-cis isomer for each name or structural formula. It is also the intent of the present inventors to claim all mixtures of the 3aS-cis and 3aR-cis isomers including the racemic mixture (1:1 ratio of 3aS-cis:3aR-cis).

Compound II of the formula,

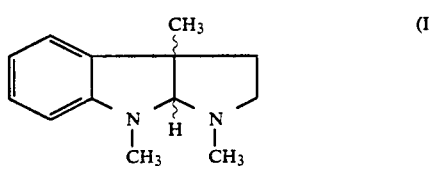

the key intermediate in the preparation of the novel compounds of the invention, is prepared utilizing generally the synthetic scheme disclosed in Julian et al., J. Chem. Soc., 1935, 563–566 and 755–757 and as outlined below:

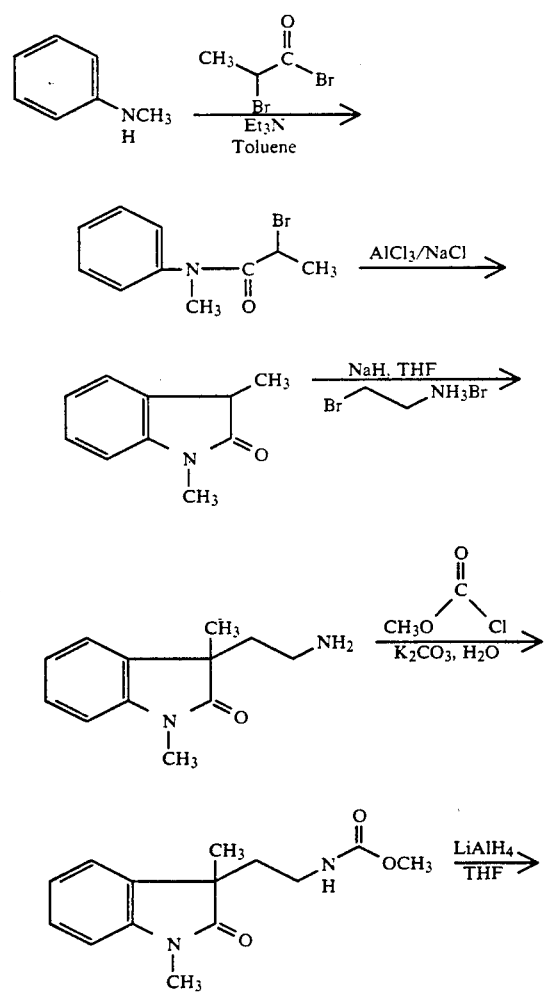

-continued

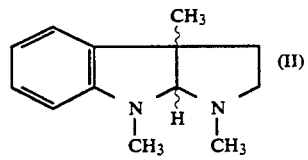

Compound II is allowed to react with pyridinium hydrobromide perbromide of the formula

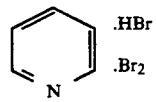

to afford Compound III of the formula

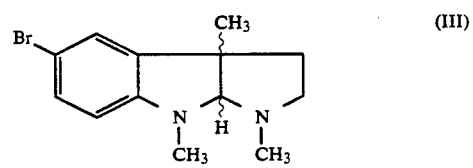

Compound III is added to a suspension of a catalytic amount of palladium acetate and tri-o-tolylphosphine which has previously been treated with isopropenyl acetate and tributyltin methoxide. The reaction of Compound III and the mixture affords the free base product, Compound IV, which is treated with a molar equivalent of di-p-toluoyl-L-tartaric acid monohydrate to afford Compound IVa of the invention of the formula

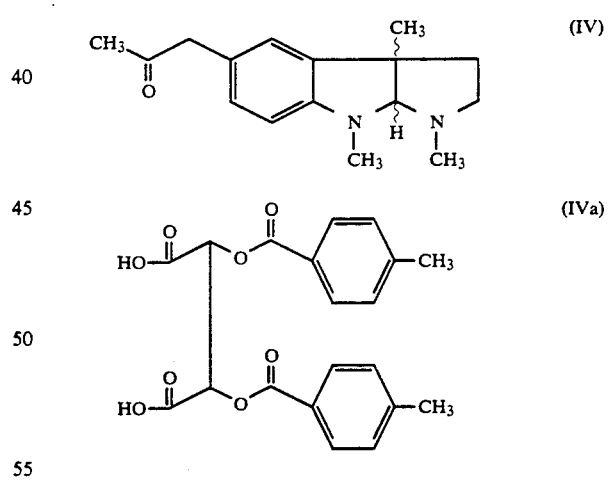

For details of the acetonylation, reference is made to Kosugi et al., Chemistry Letters, (1982), 939–940.

The formation of the free base is conducted in a hydrocarbon solvent, i.e., toluene at a temperature of 25° to 110° C. for 1 to 10 hours. The formation of the salt is conducted in an ethereal solvent, i.e., ether, at a temperature of 0° to 25° C. for 0.5 to 2 hours.

The compounds of this invention are useful in the treatment of memory impairment characterized by a cholinergic deficit such as that associated with electroshock-induced amnesia and Alzheimer's disease and other senile dementia.

This utility is manifested by the ability of these compounds to restore deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animals' initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for compounds of this invention and for tacrine and pilocarpine (reference compounds) are presented below in Table 1.

TABLE 1

| Compound | Dose (mg/kg of body-weight, s.c) | % of Animals with Scopolamine Induced Memory Deficit Reversal |
|---|---|---|
| 5-[1,2,3,3a,8,8a-hexa-hydro-1,3a,8-trimethyl-pyrrolo[2,3-b]indole acetone, di-p-toluoyl-L-tartaric acid salt | 0.3 | 27 |
|  | 1.0 | 38 |
|  | 3.0 | 31 |
| Tacrine | 0.63 | 13 |
| Pilocarpine | 5.0 | 13 |

Effective amounts of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as malic, tartaric, citric, acetic, succinic, maleic, fumaric, oxalic and salicylic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of the inventions include:

1-[1,2,3,3a,8,8a-hexahydro-1,3a,8-trimethylpyrrolo[2,3-b]indol-5-yl]-2-propanone;

1-[1,2,3,3a,8,8a-hexahydro-1,3a,8-trimethylpyrrolo[2,3-b]indol-5-yl]-2-phenylethanone;

1-[1,2,3,3a,8,8a-hexahydro-1,3a,8-trimethylpyrrolo[2,3-b]indol-5-yl]-3-phenyl-2-propanone;

1-[1,2,3,3a,8,8a-hexahydro-1,3a,8-trimethylpyrrolo[2,3-b]indol-5-yl]-3-methyl-3-phenyl-2-propanone;

1-[7-Bromo-1,2,3,3a,8,8a-hexahydro-1,3a,8-trimethylpyrrolo[2,3-b]indol-5-yl]-2-propanone;

1-[7-Chloro-1,2,3,3a,8,8a-hexahydro-1,3a,8-trimethylpyrrolo[2,3-b]indol-5-yl]-2-propanone;

1-[1,2,3,3a,8,8a-hexahydro-1,3a,8-trimethylpyrrolo[2,3-b]indol-5-yl]-1-methyl-2-propanone;

1-Bromo-1-[1,2,3,3a,8,8a-hexahydro-1,3a,8,trimethyl-pyrrolo[2,3-b]indol-5-yl]-2-propanone; and 1-[3a,8-dimethyl-1,2,3,3a,8,8a-hexahydro-1-phenylmethylpyrrolo[2,3-b]indol-5-yl]-2-propanone.

EXAMPLE 1

5-Bromo-1,2,3,3a,8,8a-hexahydro-1,3a,8-trimethylpyrrolo[2,3-b]indole

To a chilled (0° C.) solution of 1,2,3,3a,8,8a-hexahydro-1,3a,8-trimethylpyrrolo[2,3-b]indole (1.41 g) in methylene chloride (20 ml) was added pyridine (1.41 ml) under an atmosphere of $N_2$. Solid pyridinium hydrobromide perbromide (2.23 g) was added with stirring to the mixture and the resulting solution was maintained at 0° C. for 1 hour. The mixture was poured into water (100 ml) and the aqueous and organic phases separated. The organic phase was washed twice with 50 ml portions of brine and 50 ml portions of saturated sodium bicarbonate and then with 50 ml of brine. After drying the organic phase over $Na_2SO_4$ and filtering, the solvent was removed under reduced pressure. The resulting oil was purified using column chromatography on silica gel with 10% methanol in ethyl acetate as eluent. The appropriate fractions were combined, evaporated and repurified using column chromatography on silica gel with 5% methanol in ethyl acetate as eluent to afford 1.5 g of 5-bromo-1,2,3,3a,8,8a-hexahydro-1,3a,8-trimethylpyrrolo[2,3-b]indole, as an oil.

Analysis: Calculated for $C_{13}H_{17}BrN_2$: 55.53% C; 6.09% H; 9.96% N; Found: 55.33% C; 6.21% H; 9.69% N.

EXAMPLE 2

1-[1,2,3,3a,8,8a-hexahydro-1,3a,8-trimethylpyrrolo[2,3-b]indol-5-yl]-2-propanone, di-p-tolouyl-L-tartaric acid salt A stirred suspension of palladium acetate (0.18)g) and tri-O-tolylphosphine (0.49 g) in anhydrous toluene (6.0 ml) was heated to just under reflux under nitrogen for 10 minutes. The hot solution was treated, via syringe, with isopropenyl acetate (4.04 g) and tributyltin methoxide (13.0 g). After stirring for 15 minutes at this temperature, a solution of 5-bromo-1,2,3,3a,8,8a-hexahydro-1,3a,8-trimethylpyrrolo[2,3-b]indole (7.55 g) in toluene (7.0 ml) was added via canula. The mixture was refluxed for 6 hours, cooled and distilled under high vacuum to remove the toluene and methyl acetate which had formed. The crude residue was dissolved in ethyl acetate (300 ml), washed once with a 100 ml portion of brine and twice with 100 ml portions of 10% aqueous HCl. The acidic aqueous extracts were combined, cooled to 0° C. with an ice bath and made basic (pH 10) by the dropwise addition of 2N aq. NaOH solution. The free base was then extracted into ethyl acetate, washed once with a 100 ml portion of brine, dried ($Na_2SO_4$), filtered and concentrated to a syrup. This material was purified using preparative high performance liquid chromatography (HPLC) on silica gel (sample applied and eluted with 20% methanol in ethyl acetate). Concentration of the appropriate fractions afforded 1.3 g of an oil.

Analytically pure material was obtained by treating an ether solution of the oil with 1.0 equivalent of a 0.10M solution of di-p-toluoyl-L-tartaric acid monohydrate in ether. The solid which precipitated was triturated many times with diethyl ether, dried for 3 hours on a high vacuum pump and for 12 hours in a vacuum oven at 58° C. to afford 1-[1,2,3,3a,8,8a-hexahydro-1,3a,8-trimethylpyrrolo[2,3-b]indol-5-yl]-2-propanone, di-p-toluyl-L-tartaric acid salt, as a solid, m.p. 115°-125° C.

Analysis: Calculated for $C_{36}H_{40}N_2O_9$: 67.10% C; 6.25% H; 4.34% N; Found: 66.72% C; 6.34% H; 4.54% N.

We claim:

1. A compound of the formula

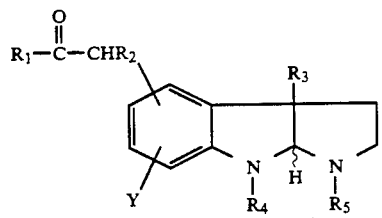

where $R_1$ is loweralkyl, aryl or arylloweralkyl; $R_2$ is hydrogen, halogen or loweralkyl; $R_3$ is hydrogen or loweralkyl; $R_4$ is loweralkyl or arylloweralkyl; $R_5$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy; or the pharmaceutically acceptable addition salts thereof, and where applicable, the geometric and optical isomers and racemic mixtures thereof.

2. The compound as defined in claim 1 which is 1-[1,2,3,3a,8,8a-hexahydro-1,3a,8-trimethylpyrrolo[2,3-b]indol-5-yl]-2-propanone, di-p-tolouyl-L-tartaric acid salt.

3. A pharmaceutical composition which comprises a compound as defined in claim 1 and a suitable carrier therefor.

4. A method of treating electroshock induced amnesia in a patient which comprises administering to said patient an effective amount of a compound as defined in claim 1.

* * * * *